United States Patent [19]
Hohlen

[11] Patent Number: 5,722,939
[45] Date of Patent: Mar. 3, 1998

[54] BODY SUPPORT LINER FOR A NECK BRACE

[75] Inventor: Linda M. Hohlen, Monticello, Minn.

[73] Assignee: Linda Hohlen, Monticello, Minn.

[21] Appl. No.: 685,818

[22] Filed: Jul. 25, 1996

[51] Int. Cl.[6] ............................................ A61F 5/00
[52] U.S. Cl. ............................................ 602/18; 602/63
[58] Field of Search .................... 602/17–19, 61–63, 602/74–77

[56] References Cited

U.S. PATENT DOCUMENTS

| | | | |
|---|---|---|---|
| 3,189,026 | 6/1965 | Barnett | 602/18 |
| 3,921,626 | 11/1975 | Neel | 602/18 |
| 4,034,747 | 7/1977 | Leroy | 602/18 |
| 5,010,877 | 4/1991 | Druskoczi | 602/18 |
| 5,295,949 | 3/1994 | Hathaway | 602/18 |

FOREIGN PATENT DOCUMENTS 1065551  11/1979  Canada ................................ 602/18

Primary Examiner—Linda C. Dvorak
Attorney, Agent, or Firm—Foley & Lardner

[57] ABSTRACT

A liner for being positioned between a person's body and a body support having a support surface for being positioned adjacent the person's body includes a fabric body configured for being coupled to the body support adjacent the body support. The fabric body is stretchable and resilient in a plurality of directions and is configured so as to wrap about and resiliently grasp the body support to maintain the body support in the shape of the body support adjacent the support surface.

34 Claims, 3 Drawing Sheets

1

BODY SUPPORT LINER FOR A NECK BRACE

BACKGROUND OF THE INVENTION

The present invention relates to supports such as slings, splints, castings, prosthetics, immobilizers and collars or braces. In particular, the present invention relates to a fabric liner for a support, wherein the fabric liner is resilient in a plurality of directions so that the fabric may be stretched to conform to the support and so that the fabric liner grasps the support in the shape of the support to maintain its positioning.

Supports such as splints, casts, prosthetics and collars or braces are universally used for a variety of purposes. For example, rigid and soft cervical collars (otherwise known as neck braces) are used for symptomatic relief of muscle, tendon, ligament, or soft tissue injury of the neck region and for post neck surgery recovery. Clavicle supports are used in the treatment of fractures of the clavicle and sometimes as an aid to posture. Knee support/immobilizers are used for varying degrees of support and/or immobilization in the management of sprains, ligamentous injuries, strains, fractures and for recuperative stages for partial or total arthroplasty. Forearm supports are used for strains, sprains, post-fractures, fractures and post-casting to provide temporary immobilization of the wrist, hand and forearm. Wrist supports are used in the management of tendonitis and carpal tunnel syndrome. In cases where the support is provided for immobilization or support, the support itself is often rigid and hard. As a result, the support is extremely uncomfortable to wear and creates abrasions and chaffing on portions of the body positioned adjacent the support.

To cushion against the rigid and hard materials forming the support, many supports are provided with nylon or foam supported between the support and the person's body. Although the cushioning makes the support more comfortable to wear, the cushioning generally does not eliminate all sharp edges protruding from the support. Furthermore, because the cushioning is compressed between the support and a person's body, the cushioning absorbs perspiration from the body. Because the cushioning is typically formed from nylon or foam, the cushioning does not readily dry out. In addition, because the cushioning is also permanently attached to the support, the cushioning is difficult to remove and is difficult to clean. Even when cleaning is possible, washing the entire brace often results in deformation of the brace or support. These problems have been particularly associated with supports such as cervical collars or neck braces which rigidly encircle and rub against the neck region.

In an attempt to cure some of the above-noted problems associated with neck braces, hospitals and neck brace manufacturers have provided ribbed cotton sleeves and Philadelphia collar liners for being positioned between the neck brace and the patient's neck. Ribbed cotton sleeves are generally unbleached, ribbed cotton sleeves which are slipped over the person's head about the person's neck prior to positioning of the neck brace about the person's neck. The ribbed cotton sleeves are generally supplied in the form of a continuous elongate tube of one by one gauge ribbed cotton which is then cut at both ends to a desired length.

Typical ribbed cotton sleeves have several disadvantages. Because the sleeve is cut at both ends, the ribbed cotton sleeve tends to fray and unravel during use. Moreover, typical ribbed cotton sleeves are extremely uncomfortable to wear and difficult to use. Although the ribbed cotton sleeve is generally stretchable in a radial direction or widthwise (course) direction to permit the ribbed cotton sleeve to be stretched over a person's head to position the sleeve about the person's neck, the ribbed cotton sleeve cannot be substantially stretched in an axial direction or lengthwise (wale) direction. Once the sleeve is stretched, the sleeve remains stretched and experiences substantial growth because the ribbed cotton sleeve lacks the necessary resilience to return to its original form unless washed. Because the ribbed cotton sleeve is not stretchable both axially and radially, the ribbed cotton sleeve does not readily conform to the neck brace. Because the ribbed cotton sleeve is not substantially resilient in both the axial and radial directions, the ribbed cotton sleeve has a tendency to become overly stretched out to create bunches of excess fabric between the neck brace and the neck. Because the ribbed cotton sleeve is not sufficiently resilient in the axial direction, the ribbed cotton sleeve cannot remain folded over corresponding ends of the neck brace. Furthermore, because the ribbed cotton sleeve is not substantially resilient in the axial direction (i.e. it has too large of a fabric stretch), the ribbed cotton sleeve cannot grasp and substantially conform to the inner surface of the neck brace which is positioned adjacent the neck. Consequently, the ribbed cotton sleeve conforms to the neck and not to the shape of the brace. As a result, the ribbed cotton sleeve does not maintain its positioning with respect to the neck brace and frequently slides downward between the neck and the neck brace to create bunches of material between the neck and the neck brace. Because the ribbed cotton sleeve often bunches and loses its position relative to the neck brace, the person wearing the ribbed cotton sleeve experiences rashes and itchiness.

In lieu of providing the ribbed cotton sleeve, some hospitals and neck brace manufacturers have alternatively provided what are known as Philadelphia collar liners. Philadelphia collar liners are specifically configured for use with Philadelphia collars which are generally comprised of a pair of opposing arcuate molded plastic plates coupled together about a patient's neck for support. Each plate has an inner surface that is generally vertically convex for fitting between a patient's chin and chest and horizontally concave for wrapping about a perimeter of the neck.

The Philadelphia collar liner generally consists of a fabric circular sheet of nylon and spandex material (commonly knows as LYCRA material) adapted for one of the two arcuate Philadelphia collar plates. To couple the sheet of nylon and LYCRA material to the arcuate Philadelphia collar plate, a strip of elastic is sewn along the edges of the fabric sheet so that the Philadelphia collar liner has the overall shape of a shower cap. The nylon LYCRA material forming the Philadelphia collar liner provides two functions. First, the nylon LYCRA material stretches in a plurality of directions for enabling the Philadelphia collar liner to be utilized with a multitude of differently sized Philadelphia collar plates. Lastly, the nylon LYCRA material of the Philadelphia collar liner enables the Philadelphia collar liner to stretch taut about the neck as the neck is positioned between the opposing concave sides of a pair of Philadelphia collar plates. Although the nylon LYCRA material stretches in a plurality of directions, the nylon LYCRA material used in the Philadelphia collar liner does not breathe. As a result, the Philadelphia collar liner does not effectively absorb and whisk away perspiration away from the neck and does not release body heat.

In use, the elastic strip of the Philadelphia collar liner is stretched about a periphery of the Philadelphia collar plate to stretch the sheet of nylon and LYCRA material across the horizontally concave surface of the Philadelphia collar plate. Because the Philadelphia collar liner is positioned and stretched across the horizontally concave Philadelphia collar plate, the Philadelphia collar liner does not substantially conform to the shape of the Philadelphia collar plate. As a result, the Philadelphia collar liner does not grasp or contact the horizontally concave surface of the Philadelphia collar plate, but only contacts the periphery of the plate. To position the Philadelphia collar plate and the Philadelphia collar liner about a patient's neck requires the sheet of nylon and LYCRA material to be pressed and stretched towards the Philadelphia collar by the patient's neck. As the patient's neck stretches the Philadelphia collar liner, the Philadelphia collar liner reciprocatively applies pressure to the neck. The resulting pressure applied to the neck by the Philadelphia collar liner constricts the neck.

Similar to the ribbed cotton sleeve, the Philadelphia collar liner also does not grasp and substantially conform to the inner generally cylindrical support surface of the neck brace that is positioned adjacent and about the neck. In contrast, the Philadelphia collar liner generally conforms to the shape and size of the neck and not to the shape and size of the neck brace support. The Philadelphia collar liner does not stretch taut adjacent the neck brace support surface but instead stretches taut about the neck. As a result, the Philadelphia collar liner is extremely uncomfortable to the patient.

SUMMARY OF THE INVENTION

The present invention is a liner for being positioned between a person's body and a body support having a support surface for being positioned adjacent the person's body. The fabric body is configured for being coupled to the body support adjacent the body support. The fabric body is stretchable and resilient in a plurality of directions and is configured so as to wrap about and resiliently grasp the body support to maintain the fabric body in the shape of the body support adjacent the support surface.

The liner of the preferred embodiment is a neck brace conforming fabric tubular sleeve. The sleeve is resilient in a plurality of directions so that end portions of the sleeve may be stretched to wrap about corresponding ends of the neck brace and so that the sleeve grasps the end portions of the neck brace to maintain the fabric sleeve in the shape of the neck brace adjacent a support surface of the neck brace. The liner is preferably formed from a fabric material having a fabric stretch in a course direction and in a wale direction wherein the fabric stretch in the course direction and the wale direction are substantially equal. Preferably, the liner is formed from a material including LYCRA.

DETAILED DESCRIPTION OF THE PREFERRED EMBODIMENTS

Figure 1:
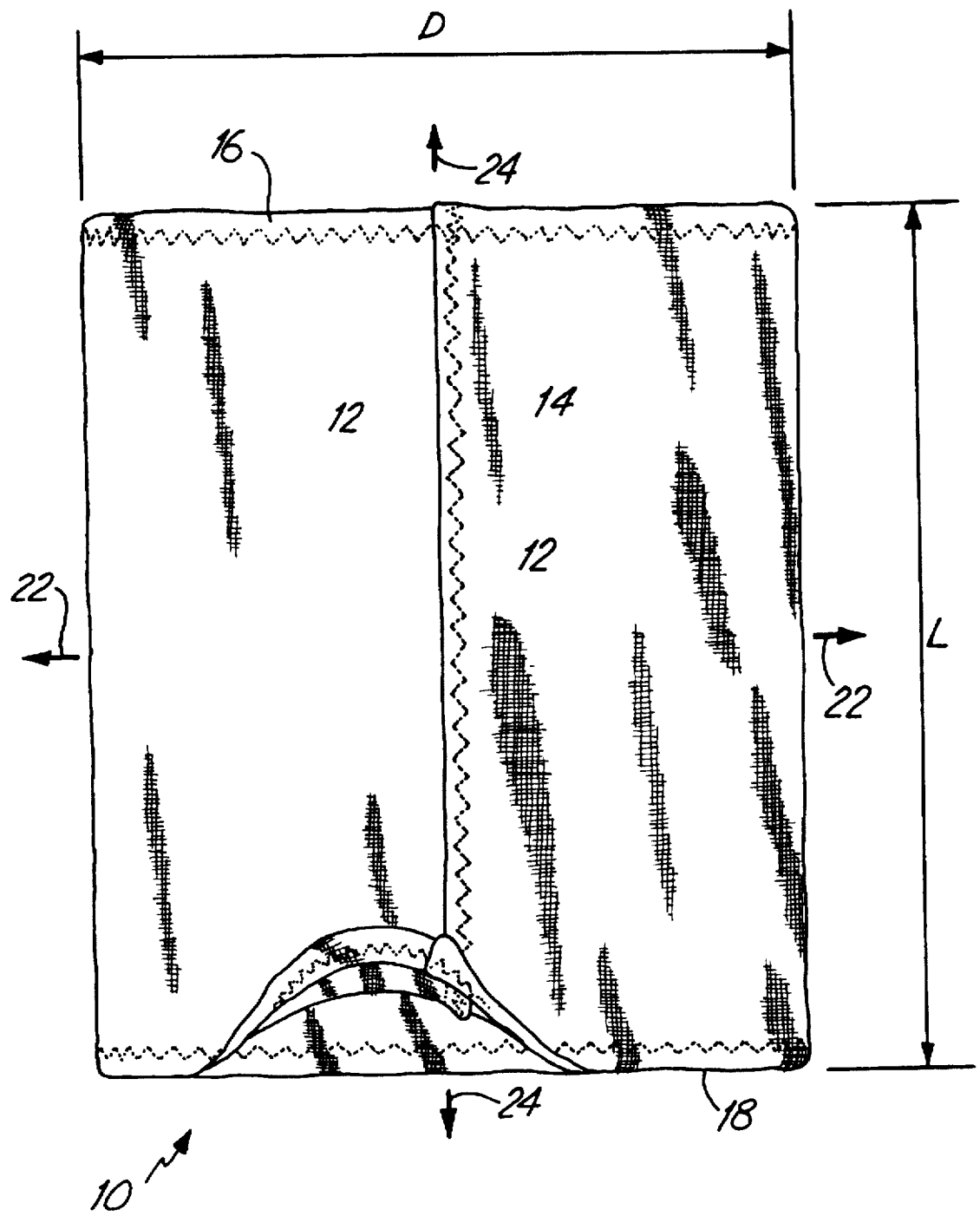
FIG. 1 is a perspective view of support liner of the present invention.

FIG. 1 is a perspective view of support liner 10. Liner 10 is generally an elongate sleeve preferably formed from a single sheet of fabric having opposite ends 12 coupled together to provide liner 10 with a tubular shaped configuration for being positioned around an anatomy such as a neck adjacent a tubular support such as a neck brace. Ends 12 are preferably sewn together to form a seam 14. Alternatively, liner 10 may be formed from a single elongate section of fabric having means for coupling opposite ends of the fabric together such as VELCRO, buttons and snaps, which enable the ends to be releasably coupled to one another to provide liner 10 with a tubular configuration for wrapping around an anatomy between the anatomy and a support such as a neck brace.

A portion of liner 10 is folded upward to illustrate an inner surface of sleeve 10 and seam 14. Seam 14 is preferably double rolled. In other words, each opposing end 12 is folded over adjacent to itself to form a folded edge. The overlapping folded portion of each end 12 are then themselves overlapped with respect to one another and stitched together to form the tubular shaped configuration of liner 10. Because seam 14 is double rolled, seam 14 is less likely to unravel and is more comfortable to the wearer because the seam is less noticeable to the wearer. Seam 14 is preferably sewn together using a stretch stitch including a plurality of stitches placed in a zig-zag orientation along the length of seam 14. Because seam 14 is stretch stitched, seam 14 maintains its integrity even when liner 10 is stretched.

As further shown by FIG. 1, top and bottom edges 16, 18 of liner 10 are also double rolled and sewn together with a stretch stitch. Consequently, top and bottom edges 16, 18 are more comfortable to the wearer and maintain their integrity during stretching of liner 10.

Liner 10 is preferably formed from a soft, smooth, breathable, moisture absorbing fabric material that is stretchable and resilient in a plurality of directions so as to stretch into conformity with a body support and so that the fabric material forming the liner sufficiently grasps the body support to maintain its position with respect to the body support. The fabric material forming liner 10 is also preferably sufficiently resilient to reliably grasp the body support and to return to its original dimensions and form after being repeatedly stretched. Preferably, liner 10 is formed from a heavy duty ten ounce weight cotton material including spandex supplied by S. R. Harris Industries in Brooklyn Park, Minn. The material chosen should preferably have sufficient amount of LYCRA material to permit the liner to stretch to approximately twice its original size. Preferably, the material chosen should have at least about five percent to about ten percent LYCRA material. Although not breathable, liner 10 may alternatively be formed from a nylon lycra/spandex material.

As shown by FIG. 1, liner 10 may be stretched both radially in a course direction as indicated by arrows 22 and axially in a wale direction as indicated by arrows 24. In addition, liner 10 is similarly resilient radially and axially so as to return to its original shape and dimensions once stretched. Table A illustrates radial (course) and axial (wale) growth and stretch properties of the preferred cotton LYCRA material forming liner 10. Table A further compares the radial (course) and axial (wale) growth and stretch properties of the preferred cotton LYCRA material forming liner 10 with the conventional ribbed cotton material typically used for neck brace liner supplied by hospitals. The test results set forth in Table A are the result of comparative stretch property tests performed in accordance with the standard testing procedure ASTM D2594-87, Section 10.2 entitled "Standard Test Methods for Stretch Properties of Knitted Fabrics Having Low Power." Pursuant to standarized testing method ASTM D2594-87, five inch gauge length samples of the preferred cotton LYCRA material forming liner 10 and the standard ribbed cotton material utilized in conventional liners were tested using a loose-fitting criteria with five pounds force and a form-fitting criteria of 10 pounds force in both the course (width) direction and the wale (length) direction for the properties of fabric growth and fabric stretch. Fabric stretch is the increase in length of a specimen of fabric resulting from a load applied under specified conditions. Fabric growth is the difference between the original length of a specimen and its length after the application of a specified load for a prescribed time and the subsequent removal of the load.

TABLE A

|  | Cotton Spandex | | Ribbed Cotton Ribbed cotton | |
| --- | --- | --- | --- | --- |
|  | Course | Wale | Course | Wale |
| Growth Test Loose-fitting criteria Fabric Growth, | | | | |
| % after 1 min. | 3.9 | 3.3 | 4.4 | 3.2 |
| % after 1 hour | 1.5 | 1.6 | 2.7 | 1.9 |
| Form-fitting criteria Fabric Growth, | | | | |
| % after 1 min. | 7.7 | 4.2 | 10.2 | 9.3 |
| % after 1 hour | 5.6 | 3.1 | 7.6 | 8.2 |
| Fabric Stretch Test | | | | |
| Loose-fitting criteria Fabric Stretch (5 lbf), % | 59.8 | 56.1 | 250. | 21.7 |
| Form-fitting criteria Fabric Stretch (10 lbf), % | 92.0 | 70.0 | 268. | 35.8 |

As shown by Table A, the preferred cotton spandex material forming liner 10 has a form fitting fabric stretch of less than about 100% in a course direction. Thus, the fabric material forming liner 10 has a sufficient resiliency in an axial direction to sufficiently grasp the support. The preferred cotton spandex material forming liner 10 also has a loose fitting fabric stretch of greater than about 50% in a wale direction. Thus, liner 10 may be sufficiently stretched in an axial direction to permit liner 10 to be wrapped about ends of the support. As further shown by Table A, the preferred cotton spandex material forming liner 10 has a one hour form-fitting fabric growth of less than 4% in a wale direction and a one hour loose- fitting fabric growth of less than about 2% in a course direction. Thus, the sleeve is less likely to become overstretched so as to create bunches of fabric between the support and the person's body. In addition, because the preferred cotton spandex material forming liner 10 has a loose-fitting fabric stretch in a course direction and a wale direction that are approximately equal (a difference of less than or equal to about 6%) and a form-fitting fabric stretch in a course direction and a wale direction that differ from one another by less than or equal to about 24%, the material stretches uniformly in a plurality of directions to provide liner 10 with better conformity to the shape of the support. Consequently, liner 10 is capable of being stretched radially as shown by arrows 22 to slide over a person's head for positioning about the person's neck. Liner 10 is also stretchable so as to stretch over and about ends of a body support such as a neck brace in close conformity with the support. Because liner 10 is configured to grasp the support in close conformity with the support, liner 10 does not apply pressure to or otherwise constrict a patient's body. Because liner 10 is also sufficiently resilient both axially and radially, liner 10 maintains its position relative to the support by grasping about ends of the support.

Figure 2:
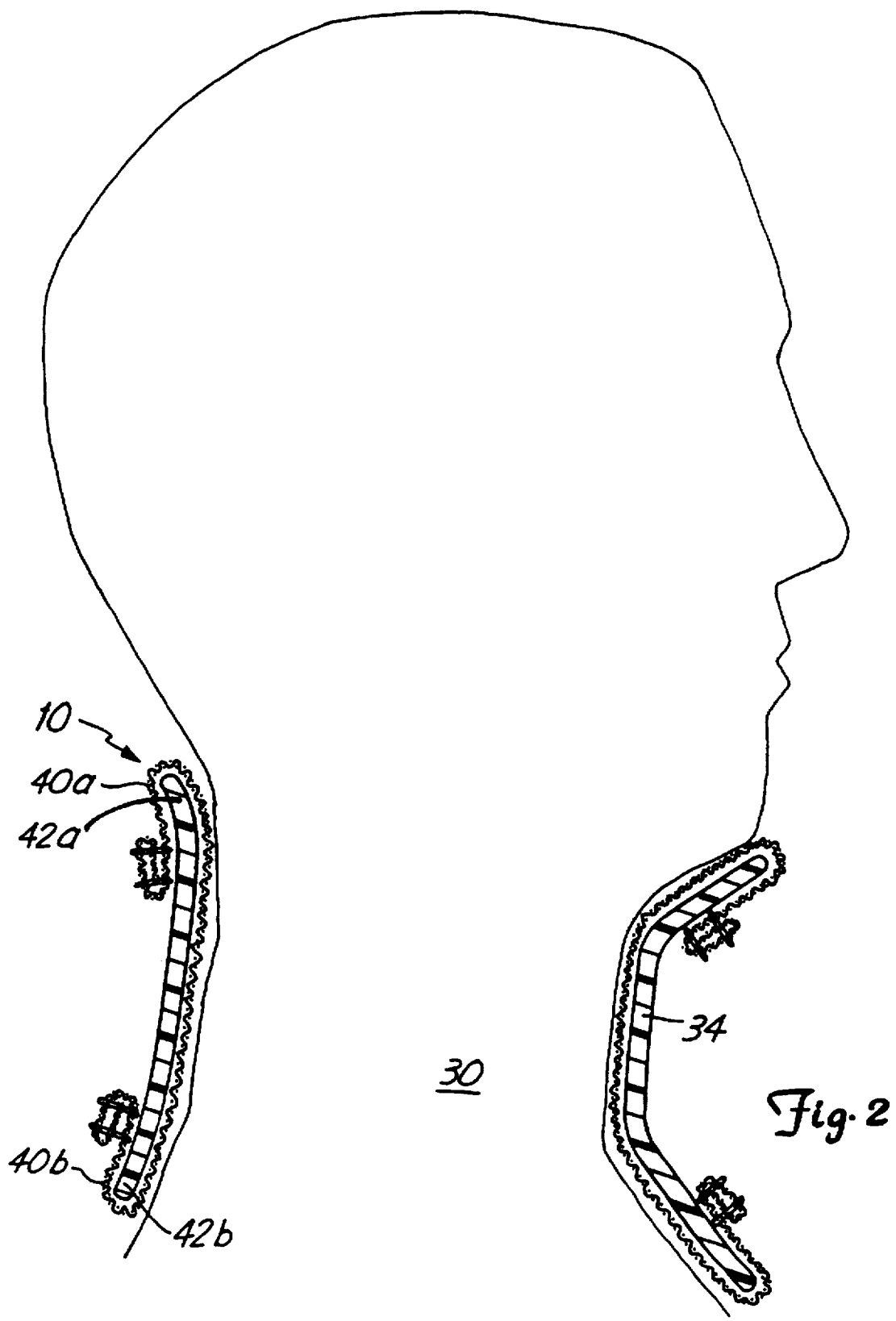
FIG. 2 is a cross-sectional view of the support liner positioned between a neck and a neck brace.

FIG. 2 illustrates liner 10 encircling a person's neck 30 between neck 30 and a conventional neck brace 34. As best shown by FIG. 2, liner 10 includes end portions 40a and 40b which are wrapped over and about corresponding end portions 42a, 42b of brace 34. End portions 40a, 40b are initially stretched over ends 42a, 42b, respectively, and resiliently grasp brace 34 to maintain the positioning of liner 10 relative to brace 34 and between neck 30 and brace 34. Because liner 10 is preferably formed from a fabric that is soft, smooth, breathable and moisture absorbing, liner 10 is comfortable to the wearer. Moreover, because liner 10 is formed from a fabric that is uniformly stretchable and resilient in a plurality of directions, liner 10 better maintains its positioning with respect to brace 34. As a result, liner 10 maintains its shape and tightness with respect to brace 34 and is less likely to slide or move relative to brace 34. Consequently, liner 10 is less likely to bunch up between neck 30 and brace 34. Because liner 10 is substantially uniformly stretchable and resilient in a plurality of directions and is configured so as to stretch into close conformity with brace 34 without pressure from neck 30, liner 10 does not apply pressure to or constrict neck 30. In particular, because liner 10 is tubular shaped, liner 10 conforms to the inner tubular shape of brace 34 without the application of pressure or force from neck 30. Furthermore, because liner 10 reliably grasps brace 34, liner 10 is less likely to accidentally expose neck 30 to brace 34. Liner 10 may also be easily removed for cleaning. Overall, liner 10 provides increased comfort to the user of the support such as a neck brace.

Figure 3:
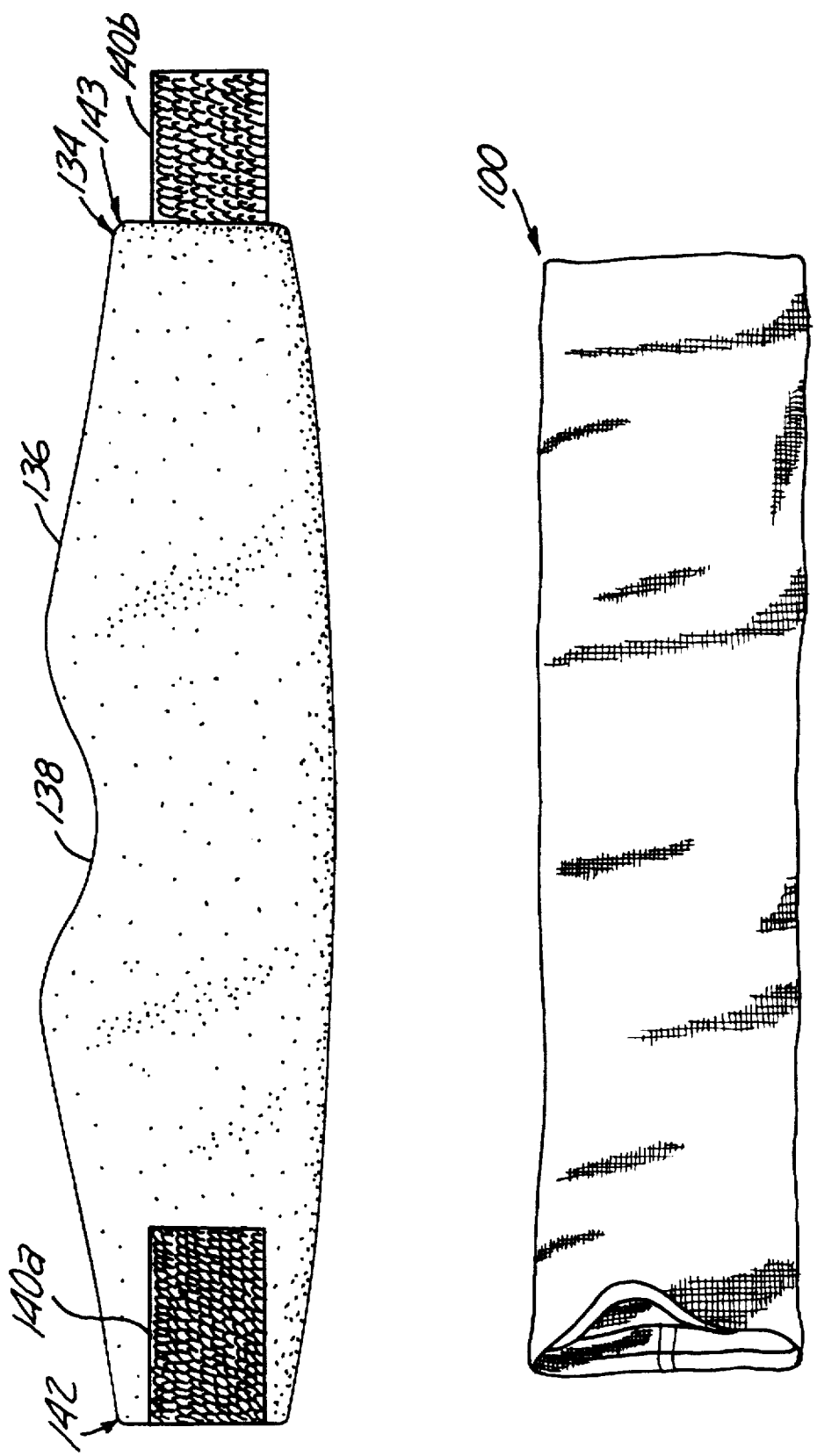
FIG. 3 is a top elevational view of a soft neck brace and an alternate embodiment of the support liner configured for use with the soft neck brace.

FIG. 3 is a top elevational view of support liner 100 configured for use with a soft neck brace or collar such as collar 134. As shown by FIG. 3, collar 134 is a standard cervical collar having hook and loop fastener (commonly known as VELCRO) ends 140a and 140b with that couple opposite ends of the collar adjacent one another about a neck. Collar 134 preferably has a central body 136 with a contour detent 138 sized for accepting a person's chin and VELCRO ends 140a, 140b. Velcro end 140a extends along end 142 adjacent to body 136. Velcro end 140b comprises a tab or strap projecting from end 143 of body 134. As conventionally known, VELCRO end 140b overlaps VELCRO end 140a to couple ends 142 and 143 of body 136 adjacent to one another about a neck.

Liner 100 is similar to liner 10 except that liner 100 is generally tubular shaped for completely wrapping about collar 134. Liner 100 preferably has a length approximately equal to or slightly less than the length of collar 134. Liner 100 preferably has an inner diameter sized for tightly receiving collar 134 so that liner 100 remains taut about collar 134 to avoid bunching up as to prevent rashes and irritations to the wearer of collar 134.

As with liner 10, liner 100 is preferably formed from a soft, smooth, breathable, moisture absorbing fabric material that is stretchable and resilient in a plurality of directions so as to stretch into conformity with the body support, namely collar 134, and so that the fabric material forming liner 100 sufficiently grasps collar 134 to maintain liner 100 in the shape of collar 134 adjacent collar 134 about a person's neck. The fabric material forming liner 100 is preferably sufficiently resilient to return to its original dimensions and form after being repeatedly stretched. Preferably, liner 100 is formed from a heavy duty type material containing spandex such as the preferred cotton spandex supplied by S. R. Harris Industries in Brooklyn Park, Minn. Alternatively, other materials containing spandex such as nylon spandex may be used to form liner 100.

In conclusion, the liner of the present invention provides a smooth, comfortable and easy to clean interfacing surface adjacent the body of the patient between the body of the patient and the particular support being used. For example, liners 10 and 100, which are specifically disclosed for use with neck braces, absorb perspiration from the neck and provide a smooth breathable cushioning surface adjacent the neck to prevent chaffing, abrasions, rashes and itchiness. At the same time, liners 10 and 100 are easily removable from the neck brace for ease of cleaning. In contrast to conventional ribbed cotton sleeves, liners 10 and 100 will remain in position with respect to the neck brace and do not bunch up. In contrast to conventional Philadelphia collar liners, liners 10 and 100 do not apply pressure to the neck or constrict the neck. In contrast to both ribbed cotton sleeves and Philadelphia collar liners, liners 10 and 100 are stretchable and resilient in a plurality of directions and are configured so as to wrap about and resiliently grasp the neck brace to maintain the liner in the shape of the neck brace adjacent the inner neck contacting surface of the neck brace. Thus, liners 10 and 100 provide the wearer of the neck brace with greater comfort.

As can be appreciated, the liner of the present invention may be reconfigured to maintain the body of the liner in the shape of a variety of different body supports adjacent the body support between the body support and the body. For example, the liner of the present invention may be reconfigured for use with such supports as clavicle supports, knee supports, forearm supports and wrist supports. By utilizing a fabric body that is stretchable and resilient in a plurality of directions and which is configured so as to wrap about and resiliently grasp the particular body support to maintain the fabric body in the shape of the particular body support adjacent the portion of the body support which would otherwise contact the body, abrasion, chaffing and discomfort to the body as well as constriction of the body may be eliminated.

Although the present invention has been described with reference to preferred embodiments, workers skilled in the art will recognize that changes may be made in form and detail without departing from the spirit and scope of the invention.

What is claimed is:

1. A liner for being positioned between a person's body and a neck brace, the neck brace having a support surface for being positioned adjacent the person's neck, a vertical length extending between an annular top edge and an annular bottom edge, the liner comprising:
    a tubular fabric body having first and second open annular end portions, wherein the fabric body is stretchable and resilient in a plurality of directions and is configured so as to have an inner diameter and a vertical height greater than the vertical length of the neck brace such that the first and second annular end portions are foldable over and about the annular top edge and the annular bottom edge of the neck brace to resiliently grasp the neck brace and maintain the fabric body in the shape of the neck brace adjacent the support surface.

2. The liner of claim 1 wherein the fabric body has a form-fitting fabric stretch of less than about 100% in a course direction.

3. The liner of claim 1 wherein the fabric body has a loose-fitting fabric stretch of greater than about 50% in a wale direction.

4. The liner of claim 1 wherein the fabric body has a form-fitting fabric stretch in both a course and a wale direction of between about 50% to about 100% in both a course direction and a wale direction.

5. The liner of claim 1 wherein the fabric body has a loose-fitting fabric stretch in both a course and a wale direction of between about 50% to about 100% in both a course direction and a wale direction.

6. The liner of claim 1 wherein the fabric body has a one hour form-fitting fabric growth of less than about 4% in a wale direction.

7. The liner of claim 1 wherein the fabric body has a one hour loose-fitting fabric growth of less than about 2.0% in a course direction.

8. The liner of claim 1 wherein the fabric body has a fabric stretch less than 100% in a course direction and greater than 50% in a wale direction.

9. The liner of claim 1 wherein the tubular fabric body has a vertical height extending between the first and second annular end portions approximately two inches greater than the vertical length of the neck brace.

10. The liner of claim 1 wherein the fabric body is formed from a material containing spandex.

11. The liner of claim 10 wherein the fabric body is formed from cotton spandex.

12. The liner of claim 1 wherein edges of the fabric body are folded and are sewn with a stretch stitch for permitting the material to stretch and grasp the body support.

13. The liner of claim 1 wherein the support comprises a neck brace and wherein the liner comprises a fabric sleeve formed by connecting opposite ends of sheet of fabric material to form a hollow tubular member and wherein each end of the sheet of fabric material is folded and sewn together after being sewn to the opposite end of the sheet of fabric material.

14. The liner of claim 1 wherein the fabric body has a loose-fitting fabric stretch in both a course direction and a wale direction and wherein the loose-fitting fabric stretch in a course direction from the loose-fitting fabric stretch in the wale direction by less than or equal to about 6%.

15. The liner of claim 1 wherein the fabric body has a form-fitting fabric stretch in a course direction and a wale direction and wherein the form-fitting fabric stretch in the course direction differs from the form-fitting fabric stretch in the wale direction less than or equal to about 24%.

16. The liner of claim 1 wherein the fabric body has a fabric stretch in a course direction and in a wale direction and wherein the fabric stretch in the course direction and the wale direction are substantially equal.

17. The liner of claim 1 wherein the fabric body has a one hour loose-fitting fabric growth less than or equal to about 1.5% in a course direction.

18. The liner of claim 1 wherein the fabric body has a form-fitting one hour fabric growth less than or equal to about 3.1% in a wale direction.

19. A liner for use with a neck brace having a vertical length extending between annular top and bottom edges and a support surface for being positioned adjacent a neck, the liner comprising:
    a neck brace conforming fabric tubular sleeve having open annular end portions, wherein the sleeve has inner diameter and is resilient in a plurality of directions so that at least one end portion of the sleeve may be stretched to fold over and wrap about the corresponding annular edge of the neck brace and so that the sleeve grasps the annular edge of the neck brace to maintain the fabric sleeve in the shape of the neck brace adjacent the support surface.

20. The liner of claim 19 wherein the fabric sleeve has a form-fitting fabric stretch of less than about 100% in a course direction.

21. The liner of claim 19 wherein the fabric sleeve has a form-fitting fabric stretch in both a course and a wale direction of between about 50% to about 100% in both a course direction and a wale direction.

22. The liner of claim 19 wherein the fabric sleeve has a loose-fitting fabric stretch in both a course and a wale direction of between about 50% to about 100% in both a course direction and a wale direction.

23. The liner of claim 19 wherein the fabric sleeve has a one hour form-fitting fabric growth of less than about 4% in a wale direction.

24. The liner of claim 19 wherein the fabric sleeve has a one hour loose-fitting fabric growth of less than about 2.0% in a course direction.

25. The liner of claim 19 wherein the fabric sleeve has a fabric stretch less than 100% in a course direction and greater than 50% in a wale direction.

26. The liner of claim 19 wherein the fabric sleeve has a vertical height extending between the open annular end portions approximately two inches greater than the vertical length of the neck brace.

27. The liner of claim 19 wherein the fabric sleeve is formed from a material including spandex.

28. The liner of claim 19 wherein the fabric sleeve is formed from cotton spandex.

29. The liner of claim 19 wherein edges of the fabric sleeve are folded and are sewn with a stretch stitch for permitting the material to stretch and grasp the body support.

30. The liner of claim 19 wherein the fabric sleeve is formed by connecting opposite ends of a sheet of fabric material to form a hollow tubular member and wherein each end of the sheet of fabric material is folded and sewn before being sewn to an opposite end of the sheet of fabric material.

31. The liner of claim 19 wherein the fabric tubular sleeve has a loose-fitting fabric stretch in both a course direction and a wale direction and wherein the loose-fitting fabric stretch in a course direction from the loose-fitting fabric stretch in the wale direction by less than or equal to about 6%.

32. The liner of claim 19 wherein the fabric tubular sleeve has a form-fitting fabric stretch in a course direction and a wale direction and wherein the form-fitting fabric stretch in the course direction differs from the form-fitting fabric stretch in the wale direction less than or equal to about 24%.

33. The liner of claim 19 wherein the fabric tubular sleeve has a fabric stretch in a course direction and in a wale direction and wherein the fabric stretch in the course direction and the wale direction are substantially equal.

34. The liner of claim 19 wherein the fabric tubular sleeve has a one hour loose-fitting fabric growth less than or equal to about 1.5% in a course direction.

* * * * *